(12) United States Patent
Kaiser et al.

(10) Patent No.: US 6,974,420 B2
(45) Date of Patent: Dec. 13, 2005

(54) METHOD AND APPARATUS FOR REDUCING NOISE AND DETECTING ELECTRODE FAULTS IN MEDICAL EQUIPMENT

(75) Inventors: Wilhelm J. Kaiser, Emmendingen (DE); Horst Weber, Freiburg (DE); Wolfgang Winter, March (DE)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 550 days.

(21) Appl. No.: 10/200,411

(22) Filed: Jul. 22, 2002

(65) Prior Publication Data

US 2002/0183797 A1 Dec. 5, 2002

Related U.S. Application Data

(62) Division of application No. 09/576,304, filed on May 23, 2000, now Pat. No. 6,487,449.

(51) Int. Cl.$^7$ .............................. A61B 5/05; A61N 5/04
(52) U.S. Cl. ....................... 600/554; 600/508; 600/547
(58) Field of Search .................. 607/28, 119, 121–123, 607/142, 152, 25, 17–19; 600/509, 513, 547, 600/554

(56) References Cited

U.S. PATENT DOCUMENTS

| | | | |
|---|---|---|---|
| 3,602,215 A | 8/1971 | Parnell | 600/508 |
| 4,919,145 A | 4/1990 | Marriott | 600/536 |
| 4,951,682 A * | 8/1990 | Petre | 600/526 |
| 5,231,990 A | 8/1993 | Gauglitz | 600/510 |
| 5,632,280 A | 5/1997 | Leyde et al. | 600/508 |
| 5,649,969 A | 7/1997 | Abrahamson et al. | 607/28 |
| 5,650,750 A | 7/1997 | Leyde et al. | 330/2 |
| 5,755,744 A | 5/1998 | Shaw et al. | 607/45 |
| 5,921,939 A | 7/1999 | Danielsson et al. | 600/509 |
| 6,278,894 B1 * | 8/2001 | Salo et al. | 600/547 |

FOREIGN PATENT DOCUMENTS

WO  WO 83/01374  4/1983 ............ A61B 5/02

OTHER PUBLICATIONS

John G. Webster, Editor; Medical Instrumentation-Application and Design, John Wiley & Sons, Inc., New York, (3rd Ed. 1998) pp. 276- 277.

* cited by examiner

Primary Examiner—Carl H. Layno
(74) Attorney, Agent, or Firm—Andrus, Sceales, Starke & Sawall, LLP

(57) ABSTRACT

A method and apparatus for reducing noise and detecting electrode faults in a physiological activity acquisition system. The method includes the act of delivering a carrier signal through an electrode connected to a subject. Once the carrier signal is delivered, a combined signal having an electrical-activity portion and a carrier-signal portion is sensed by at least one signal sensing electrode attached to the subject. A low-pass, finite impulse response filter, having a first zero point frequency substantially the same as the carrier signal, separates the carrier signal portion from the electrical activity portion. An impedance value for the sensing electrode is calculated using the carrier signal portion. The calculated impedance value is compared against a known value to determine whether an electrode fault exists.

16 Claims, 3 Drawing Sheets

ELECTRODE FAULTS

METHOD AND APPARATUS FOR REDUCING NOISE AND DETECTING ELECTRODE FAULTS IN MEDICAL EQUIPMENT

The present application is a divisional of co-pending U.S. patent application Ser. No. 09/576,304 filed May 23, 2000, now U.S. Pat. No. 6,487,449, and is hereby incorporated by reference herein.

BACKGROUND OF THE INVENTION

The present invention relates to a method and apparatus for reducing noise and detecting electrode faults in equipment used to measure physiological activity.

Organ function in humans and other subjects is often controlled or otherwise associated with electrical activity. For example, human and animal nervous systems generate a variety of electrical signals that can be monitored and measured. Similarly, the rhythmic beating of a heart is maintained by an orderly series of electrical discharges. In humans, the discharges originate in the sinus node of the right atrium. The discharges proceed through the atrioventricular node and a bundle of neuromuscular fibers (known as the bundle of His) to the ventricles. By attaching electrodes to various parts of the body, a record of the electrical activity of the heart can be obtained. This record is known as an electrocardiogram or ECG. ECGs are used in a variety of diagnostic and treatment procedures.

The correct application of electrodes to a patient is very important to proper detection and measurement of ECGs. If an electrode is improperly or poorly connected to the body, either no ECG signal or a noisy ECG signal is detected. This can result in misdiagnoses and improper medical treatment, which in turn can have serious consequences.

To avoid erroneous ECG readings, a number of devices and methods have been developed to detect or to identify electrode fault conditions. Despite the existence of these devices and methods, adequate detection of electrode faults and reduction of the noise associated with electrode faults and poor electrode connections has not been achieved.

SUMMARY OF THE INVENTION

The present invention provides a method and an apparatus for detecting faults in electrodes used to measure electrical activity in subjects. The invention also provides a mechanism for reducing noise in signals from electrodes. The method includes the acts of delivering a carrier signal to the subject by connecting an RL electrode (so named because it is generally positioned over or near the right leg) to the subject. The RL electrode delivers an AC carrier signal to the subject. Once the RL signal is delivered to the subject, a combined signal having an electrical-activity portion and a carrier-signal portion is sensed by attaching at least one signal sensing electrode to the subject. The combined signal is then processed by dividing the electrical activity portion from the carrier signal portion. An impedance value for the at least one signal sensing electrode is then calculated using the carrier signal portion. Finally, the calculated impedance value is compared against known values to determine whether an electrode fault exists.

Preferably, the act of processing the combined signal includes filtering the combined signal in a low-pass, finite impulse response filter having a first zero point frequency. The low-pass filter is used to reduce high frequency noise and to separate the sensed carrier signal portion from the sensed electrical activity portion. The low-pass filter is also used to determine the characteristics of the carrier signal. In particular, the carrier signal is generated so that it has a frequency substantially the same as the first zero point frequency of the filter. Since the filter is used for two functions, namely noise filtering and removing the carrier signal, less computing power is needed in the present invention as compared to prior-art electrode fault detecting systems. Using less computing power is particularly beneficial in multi-lead systems with 12 or more leads.

The invention may be implemented in a system that includes a first ECG signal sensing electrode, a second ECG signal sensing electrode, and a third ECG signal sensing electrode, all of which are designed to be attached to a patient or subject. An RL electrode is also connected to the patient. The RL electrode carries an AC carrier signal generated by a signal generator. The carrier signal radiates from the RL electrode and is sensed, along with physiological electrical activity from the patient, by the sensing electrodes. Thus, each sensing electrode outputs a combined signal having a carrier signal portion and an electrical activity portion. The signals from the electrodes are delivered to a signal processing unit that processes the signals and generates an output signal that may be delivered to a device such as a monitor, a printer, or additional processing device. The signal processing unit also generates an electrode fault signal that may be delivered to a control or warning device to trigger an alarm indicator, such as a light or audio alarm.

As is apparent from the above, it is an advantage of the present invention to provide a method and system of identifying faults in electrodes in combination with noise filtering. Other features and advantages of the present invention will become apparent by consideration of the detailed description and accompanying drawings.

DETAILED DESCRIPTION

Figure 1:
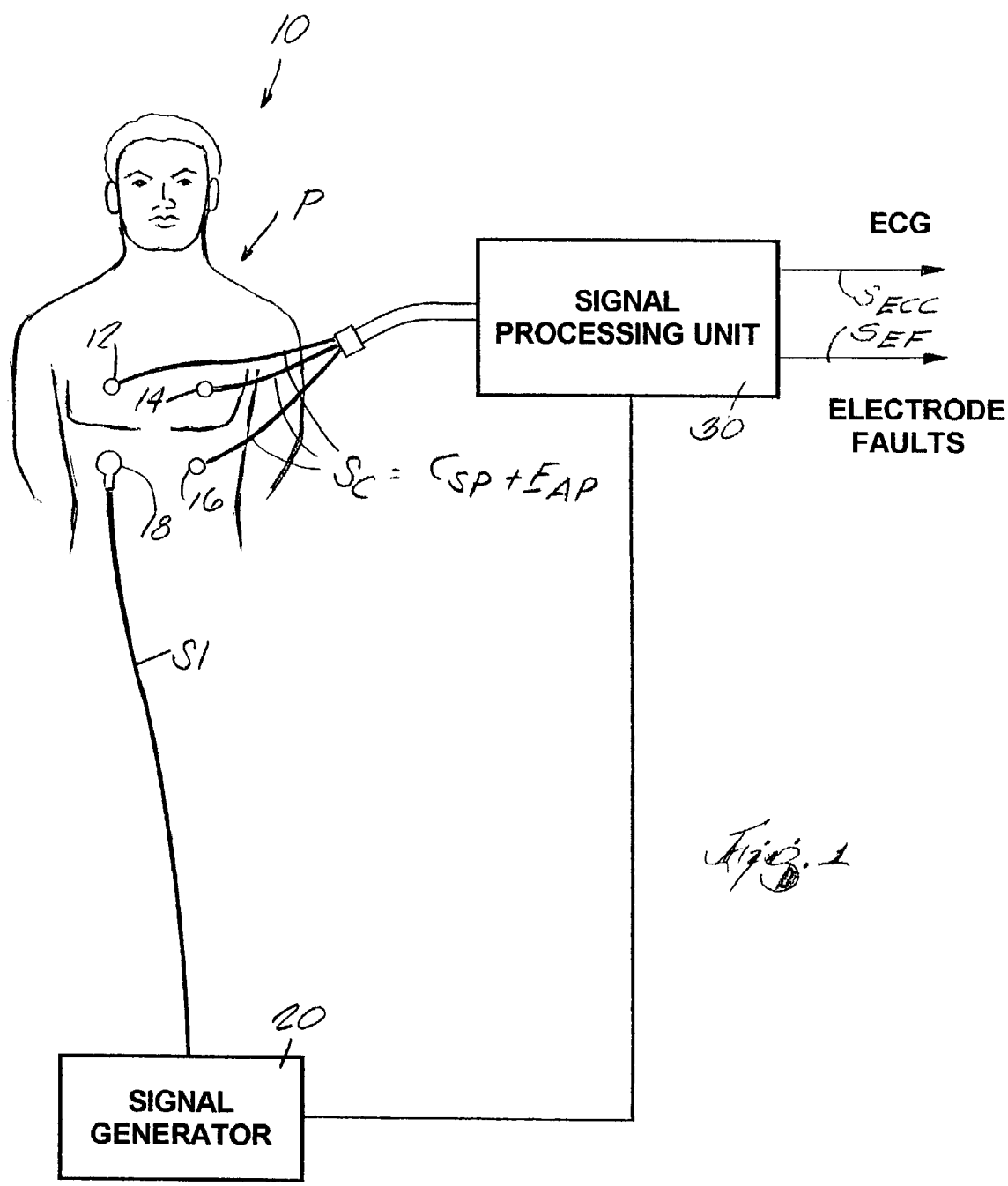
FIG. 1 is a schematic diagram of an apparatus embodying the invention.

Before one embodiment of the invention is explained in detail, it is to be understood that the invention is not limited in its application to the details of the construction and the arrangements of the components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

FIG. 1 illustrates a system 10 embodying the invention. The system 10 acquires and filters ECG signals from a living subject, such as a human patient P, and detects electrode faults occuring during the acquisition of the signal. The system 10 includes a first ECG signal sensing electrode 12, a second ECG signal sensing electrode 14, and a third ECG signal sensing electrode 16. The electrodes 12, 14, and 16 need not be of any special type, but may be any common electrode used to measure ECG and similar electrical signals. The electrodes may be attached or otherwise connected to the patient P in accordance with known methods. While only three electrodes are shown, fewer or more electrodes may be connected to the patient.

A right leg (RL) electrode 18 is also connected to the patient. While it is preferred that an RL electrode be used in the invention, it should be understood that other active electrodes capable of sending a signal could be used. The RL electrode carries an alternating-current carrier signal S1 generated by a signal generator 20. The signal S1 radiates from the electrode 18 and is sensed, along with physiological electrical activity from the patient P by the sensing electrodes 12, 14, and 16. Thus, each sensing electrode outputs a combined signal $S_C$ having a carrier signal portion $C_{SP}$ and an electrical activity portion $E_{AP}$. The signals $S_C$ are delivered to a signal processing unit 30. The processing unit 30 processes the signals and generates a noise reduced ECG output signal $S_{ECG}$. The signal $S_{ECG}$ may be delivered to a device such as a monitor, a printer, or additional processing device (none of which are shown). The signal processing unit 30 also generates an electrode fault signal $S_{EF}$ that may be delivered to a control or warning device to trigger an alarm indicator (not shown), such as a light or audio alarm.

Figure 2:
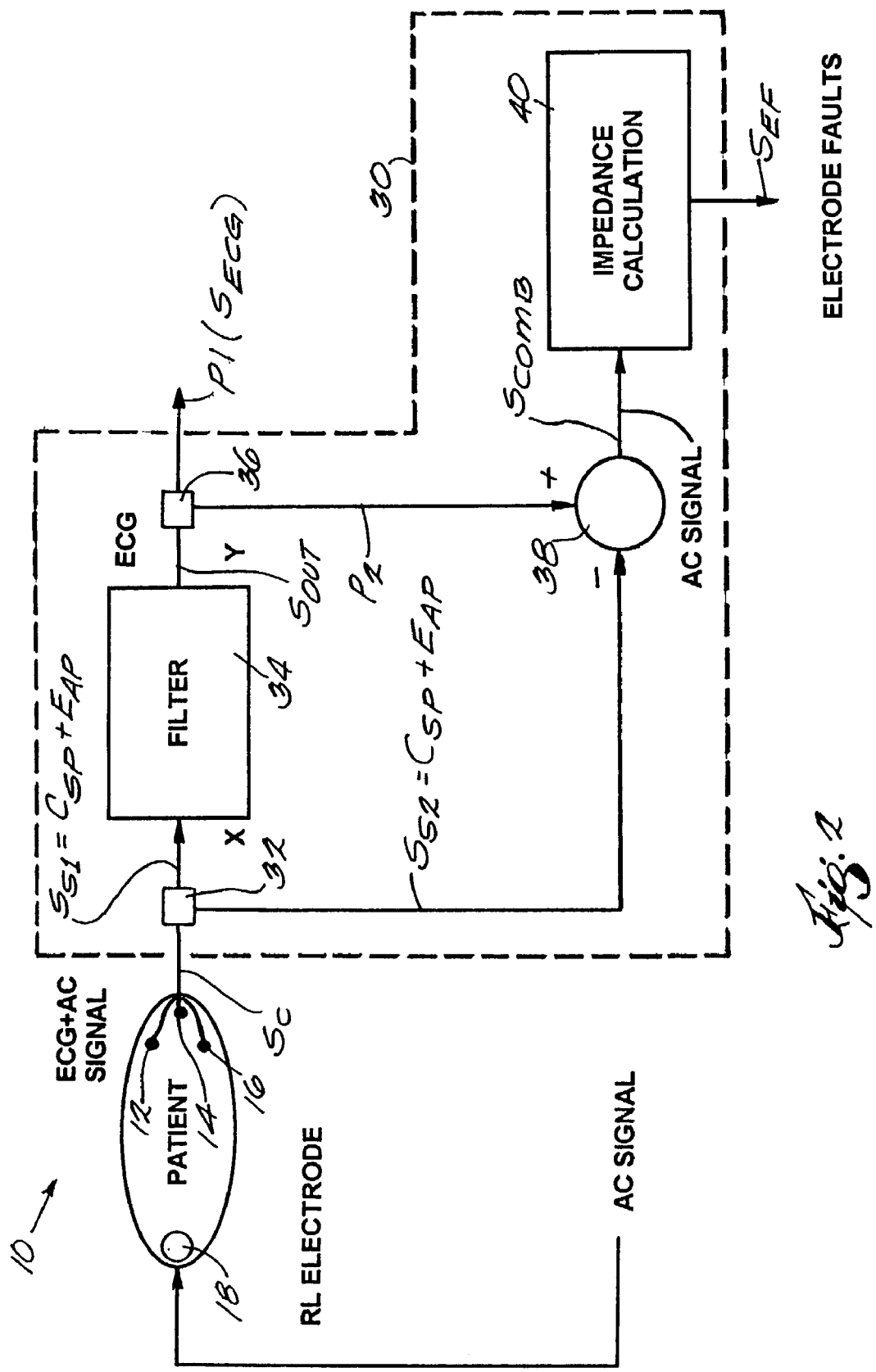
FIG. 2 is schematic diagram of a signal processing unit embodying the invention.

As best shown in FIG. 2, the signal processing unit 30 includes a splitter 32. The signals $S_C$ are split by the splitter 32 into a first signal part $S_{S1}$ and a second signal part $S_{S2}$. The first signal part $S_{S1}$ is delivered to a filter 34. The filter 34 reduces the high frequency noise in the first signal part $S_{S1}$. The filter 34 also filters out substantially all of the carrier signal portion $C_{SP}$ from the first signal part $S_{S1}$ and outputs a signal $S_{OUT}$ containing the electrical activity portion $E_{AP}$. The signal $S_{OUT}$ is sent to a second splitter 36. The splitter 36 divides the signal $S_{OUT}$ into a first signal, which is the signal $S_{ECG}$, and a second signal P2. The second signal P2 is sent to the positive input of a summing node or combiner 38.

The signal $S_{S2}$ from the splitter 32 is also delivered to the combiner 38. In particular, the signal $S_{S2}$ is sent to the negative input of the combiner. The signals P2 and $S_{S2}$ are combined in the combiner 38 such that the electrical activity portions of each signal are substantially cancelled (reduced to a zero or near zero amplitude). The combiner outputs a signal $S_{COMB}$ that includes the carrier portion $C_{SP}$ from the signal $S_{S2}$. The signal $S_{COMB}$ is input to an impedance calculator 40. The impedance calculator 40 uses the signal $S_{COMB}$ to calculate impedance values for each electrode 12–16. The impedance calculator 40 compares the calculated values against known impedance values for each electrode. The impedance calculation is based on the impedance between the electrode and the subject's skin surface. If a sensing electrode is properly applied or connected to the subject, the amplitude of the carrier signal portion $C_{SP}$ is relatively low. If a sensing electrode has an internal defect or is improperly connected, the amplitude of the carrier signal $C_{SP}$ is relatively high.

Figure 3:
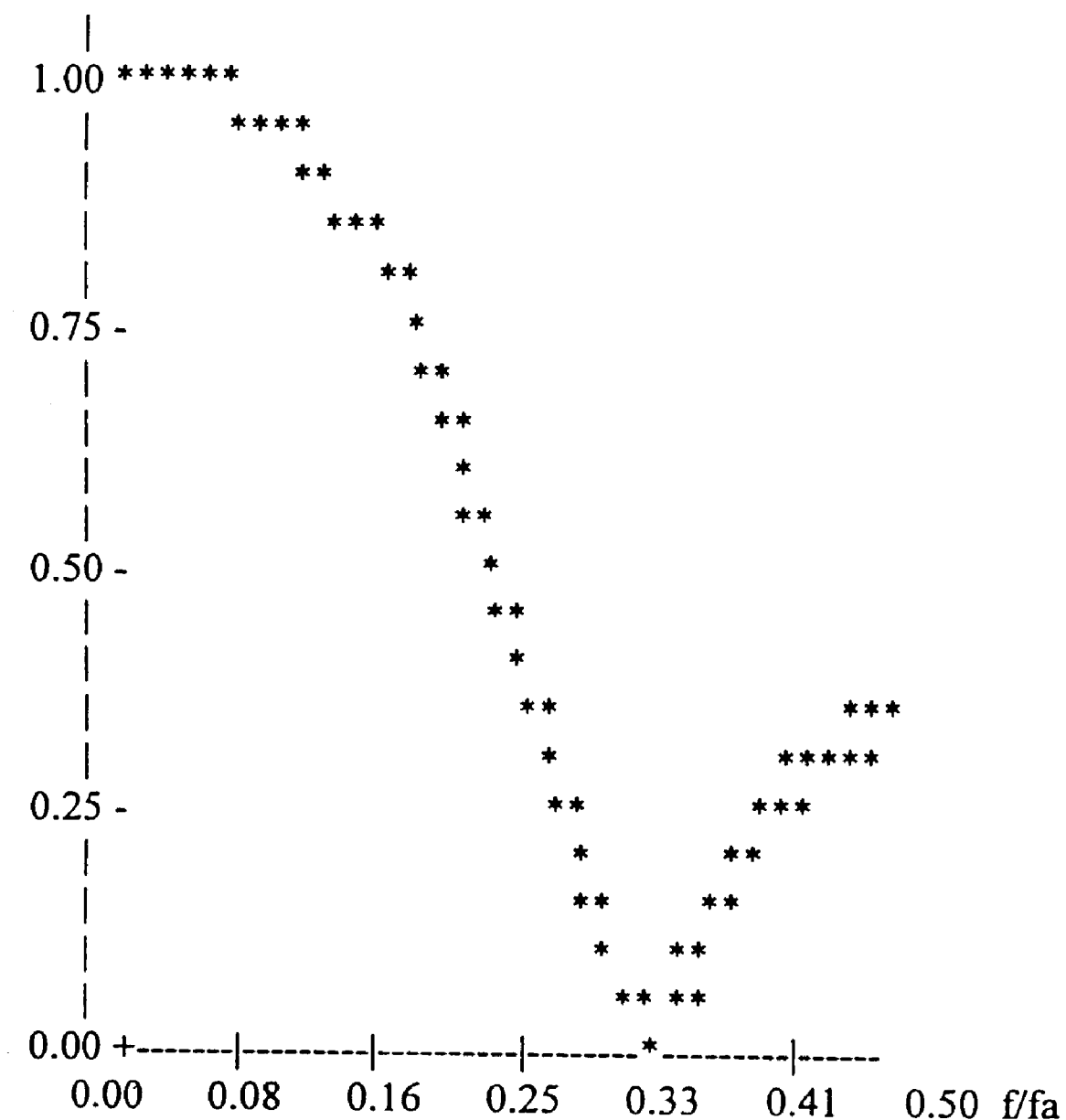
FIG. 3 is a diagram of the frequency response of a low pass-filter suitable for use in the invention.

The impedance value for each electrode (the impedance between the electrode and the skin of the subject) is determined in a four-step algorithm using both the filter 34 and the impedance calculator 40. In the first step, the first signal part $S_{S1}$ is filtered using the filter 34, as noted above. In the preferred embodiment, the filter 34 is a low-pass, finite impulse response (FIR) filter. As is known in the art, an FIR filter is implemented using software and can be characterized by the following equation:

$$y=(x_n+x_{n1}+\ldots +x_{n-N+1})/N \qquad \text{Eqn. 1}$$

where x is the input signal, y is the output signal, and N is the number of x input terms. For ECG acquisition applications, it is preferred that the filter 34 have a cut-off or corner frequency (−3 dB) of about 150 Hz. With a sampling rate of 1000 Hz, N is equal to three. Substituting these values into Eqn. 1, the first zero point (the first point at which a frequency is completely suppressed) is about 333 Hz. This is illustrated in the frequency response graph shown in FIG. 3. As shown, at about 333 Hz, the filter has a gain of zero.

The filter 34 outputs the signal $S_{OUT}$. $S_{OUT}$ can be described by $$S_{OUT}[i]=(S_{S1}[i]+S_{S1}[i-1]+S_{S1}[i-2])/3 \qquad \text{Eqn. 2}$$

When the frequency of the carrier signal S1 is set to the frequency of the first zero point of the filter 34, the mere act of filtering removes the carrier signal or carrier signal portion $C_{SP}$ from the signal $S_{S1}$, with the result that the signal $S_{OUT}$ contains only the electrical activity portion $E_{AP}$. In the next step of the algorithm, signal P2 is subtracted from the signal $S_{S2}$ at the combiner 38 to generate the signal $S_{COMB}$, which can be described by $$S_{COMB}[i]=S_{S2}[i]-P2[i] \qquad \text{Eqn. 3}$$

In the third step, the differential of signal $S_{COMB}$ is calculated in the impedance calculator 40 to yield $$S4[i]=S_{COMB}[i]-S_{COMB}[i-1] \qquad \text{Eqn. 4}$$

Differentiation results in an amplification of the signal $S_{COMB}$. In the fourth step, the signal S4 is used to calculate the impedance value by adding the absolute values of three values of signal S4 according to $$S5[i]=(|S4[i]|+|S4[i-1]|+|S4[i-2]|)/6 \qquad \text{Eqn. 5}$$

Taking the absolute values for signal S4 makes the signal S5 independent of the phase between the signal S4 and the sampling rate. If a calculated impedance value differs from a known impedance value by a predetermined amount, such as 10% or more, a fault is detected and the impedance calculator generates the electrode fault signal $S_{EF}$.

As noted, the signal generator 20 is adjusted so that the frequency of the carrier signal S1 matches the first zero point of the filter 34. Since the filter 34 is used to filter the electrical activity signal $S_{S1}$ and to extract the AC carrier signal that is fed to the RL electrode 18, less computing resources are required in the present invention than in prior systems. In prior systems, two separate sets of computer or programmatic calculations must be carried out. Using less computing resources is important in multi-lead systems because as the number of leads increases, the amount of computing power necessary to process the signals from the leads increases. While high-power computers and processors are available, high-power computers are relatively expensive. Being able to produce an effective system with an inexpensive computer helps keep the cost of the system 10 low.

As can be seen from the above, the invention provides a method and system for determining or identifying electrode faults in a physiological sensing system.

Various features and advantages of the invention are set forth in the following claims.

What is claimed is:

1. A method of identifying an electrode fault in a system designed to measure electrical activity of a subject, the method comprising:

delivering a carrier signal to the subject by connecting a first electrode to the subject;

sensing a combined signal having an electrical-activity portion and a carrier-signal portion by attaching at least one signal sensing electrode to the subject;

processing the combined signal detected by the sensing electrode by dividing the electrical activity portion from the carrier signal portion;

calculating an impedance value for the at least one signal sensing electrode; and determining whether the calculated impedance for the at least one sensing electrode exceeds a predetermined value.

2. A method as claimed in claim 1, further comprising reducing high-frequency noise of the electrical activity portion of the combined signal.

3. A method as claimed in claim 1, wherein processing the combined signal detected by the sensing electrode includes filtering the combined signal in a low-pass filter with a first zero point frequency, and wherein the carrier signal has a frequency substantially the same as the first zero point frequency.

4. A method as claimed in claim 3, wherein the low-pass filter is a finite-impulse response filter.

5. A method as claimed in claim 4, wherein the low-pass filter has a cut-off frequency of about 150 Hz.

6. A method as claimed in claim 4, wherein calculating an impedance value involves using the carrier-signal portion.

7. A method as claimed in claim 1, wherein the combined signals are sensed by attaching multiple sensing electrodes to the subject.

8. A method of identifying an electrode fault in a system designed to measure electrical activity of a subject, the method comprising:

delivering a carrier signal to the subject by connecting a first electrode to the subject;

sensing a combined signal having an electrical-activity portion and a carrier-signal portion by attaching at least one signal sensing electrode to the subject;

filtering the combined signal detected by the at least one signal sensing electrode with a low-pass filter having a zero point frequency; and calculating the frequency of the filtered carrier-signal portion based on the zero-point frequency of the low-pass filter.

9. A method as claimed in claim 8, further comprising:

identifying an impedance value for the at least one signal sensing electrode; and determining whether the calculated impedance for the at least one sensing electrode exceeds a predetermined value.

10. An apparatus for detecting an electrode fault, the apparatus comprising:

a signal processor;

a carrier signal generator;

at least one physiological activity electrode to sense a signal and coupled to the signal processor;

a carrier signal electrode coupled to the signal processor and the carrier signal generator; and a filter to remove a carrier signal from the signal sensed by the at least one physiological electrode, wherein the filter is a low-pass filter, and wherein the low-pass filter is a finite impulse response filter with a first zero point frequency.

11. An apparatus as claimed in claim 10, wherein the low-pass filter is used to determine the characteristics of the carrier signal.

12. An apparatus for detecting an electrode fault, the apparatus comprising:

a carrier signal generator operable to generate a carrier signal having a frequency; and a signal processor operable to be coupled to at least one physiological activity electrode and a carrier signal electrode, the at least one physiological activity electrode operable to sense a signal having an electrical activity portion and a carrier signal portion, the signal processor having a filter operable to reduce high frequency noise in the signal and to separate the carrier signal portion from the electrical activity portion, the filter having a first zero point frequency that is substantially the same as the frequency of the carrier signal.

13. The apparatus as claimed in claim 12, wherein the filter is a finite impulse response filter with corner frequency of 150 Hertz.

14. The apparatus as claimed in claim 12, wherein the carrier signal electrode is connected to the right leg of a subject.

15. The apparatus as claimed in claim 12, further comprising:

a visual alarm activated by an electrode fault signal from the signal processor.

16. The apparatus as claimed in claim 12, further comprising:

an audible alarm activated by an electrode fault signal from the signal processor.

* * * * *